United States Patent [19]

Lee et al.

[11] Patent Number: 4,563,310

[45] Date of Patent: Jan. 7, 1986

[54] PHENOXYPHENYL PHOSPHINATES

[75] Inventors: Shy-Fuh Lee, Sunnyvale; Clive A. Henrick, Palo Alto, both of Calif.

[73] Assignee: Zoecon Corporation, Palo Alto, Calif.

[21] Appl. No.: 580,768

[22] Filed: Feb. 16, 1984

Related U.S. Application Data

[63] Continuation of Ser. No. 369,306, Apr. 16, 1982, abandoned, which is a continuation-in-part of Ser. No. 340,580, Jan. 18, 1982, abandoned, which is a continuation-in-part of Ser. No. 276,444, Jun. 22, 1981, abandoned, which is a continuation-in-part of Ser. No. 272,422, Jun. 10, 1981, abandoned, which is a continuation-in-part of Ser. No. 264,259, May 18, 1981, abandoned.

[51] Int. Cl.$^4$ .................................................. C07F 9/32
[52] U.S. Cl. ................................ 260/941; 260/940; 260/950; 260/951; 260/948
[58] Field of Search ............... 260/951, 502.4 R, 941, 260/940, 948, 950, 455 P; 546/24

[56] References Cited

U.S. PATENT DOCUMENTS

| | | | |
|---|---|---|---|
| 4,322,375 | 3/1982 | Maier et al. | 260/951 |
| 4,419,123 | 12/1983 | Swithenbank | 260/951 |
| 4,419,124 | 12/1983 | Swithenbank | 260/951 |
| 4,456,465 | 6/1984 | Lee | 260/951 |

FOREIGN PATENT DOCUMENTS

| | | | |
|---|---|---|---|
| 0043801 | 1/1982 | European Pat. Off. | |
| 65374 | 11/1982 | European Pat. Off. | 260/951 |

OTHER PUBLICATIONS

Abstract of Japanese J 57-048-990, 3/1982.

*Primary Examiner*—Anton H. Sutto
*Attorney, Agent, or Firm*—Hana Dolezalova; Jacqueline S. Larson

[57] ABSTRACT

Novel phenoxy-, phenylthio, anilino-, benzyl-, pyridyloxy-, pyridylthio-, pyridylamino-, or pyridylmethylphenyl substituted phosphinates and phosphinothioates, synthesis thereof, intermediates therefore, and the use of said novel compounds for the control of weeds.

10 Claims, No Drawings

PHENOXYPHENYL PHOSPHINATES

This is a continuation of Ser. No. 369,306, filed Apr. 16, 1982, which is a continuation-in-part of Ser. No. 340,580, filed Jan. 18, 1982, which is a continuation-in-part of Ser. No. 276,444, filed on June 22, 1981, which is a continuation-in-part of Ser. No. 272,422, filed on June 10, 1981, which is a continuation-in-part of Ser. No. 264,259, filed May 18, 1981, the entire disclosure of which are incorporated herein by reference, all now abandoned.

The present invention relates to novel phenoxy-, phenylthio-, anilino-, benzyl-, pyridyloxy-, pyridythio-, pyridylamino-, or pyridylmethyl-phenyl substituted phosphinates and phosphinothioates, synthesis thereof, intermediates therefor, and the use of said novel compounds for the control of weeds.

More particularly, the novel compounds of the present invention are represented by the following formula (C):

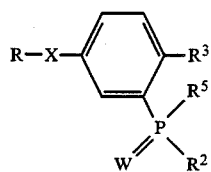
(C)

wherein:
R is the group

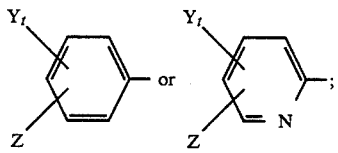

W is oxygen or sulfur;
X is oxygen, sulfur, amino or methylene;
Y is hydrogen, lower alkyl, lower alkoxy, lower haloalkyl, lower haloalkoxy, halogen, cyano or nitro;
Z is independently selected from the values of Y;
t is zero, one or two;
$R^2$ is hydrogen, lower alkyl or aryl;
$R^3$ is cyano, nitro, amino or chloro;
$R^5$ is lower alkyl, —$OR^6$, —$SR^7$, or —$NHR^8$;
$R^6$ is hydrogen, lower alkyl, lower haloalkyl, lower alkenyl, lower alkynyl, substituted or unsubstituted aryl, substituted or unsubstituted benzyl, lower alkoxyalkyl, substituted or unsubstituted phenoxyalkyl, lower alkylthioalkyl, substituted or unsubstituted phenylthioalkyl, lower alkylcarbonylalkyl, lower alkylsulfonylalkyl, substituted or unsubstituted phenylsulfonylalkyl, dialkylaminoalkyl, heterocycloalkyl, heterocycloalkalkyl, or the group

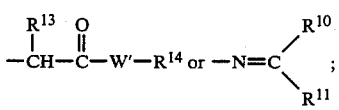

$R^7$ is hydrogen, lower alkyl, lower haloalkyl, lower alkenyl, lower alkynyl, aryl, or the group

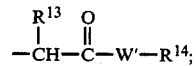

$R^8$ is hydrogen, lower alkyl, lower haloalkyl, lower alkenyl, lower alkynyl, aryl, or the group —$OR^{12}$ or

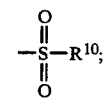

W' is oxygen, sulfur or $NR^{15}R^{16}$;
$R^{10}$ is lower alkyl;
$R^{11}$ is lower alkyl, or together with $R^{10}$ forms a lower cycloalkyl ring;
$R^{12}$ is lower alkyl, lower alkenyl or lower alkynyl;
$R^{13}$ is hydrogen, lower alkyl, lower alkoxy or lower alkylthio;
$R^{14}$ is hydrogen, Na+, lower alkyl, lower haloalkyl, lower cyanoalkyl, lower alkenyl, lower haloalkenyl, lower alkynyl, lower alkylcarbonyl, phenyl, substituted phenyl, benzyl, or the group

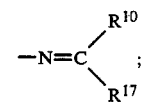

$R^{15}$ is hydrogen or lower alkyl;
$R^{16}$ is hydrogen, lower alkyl or phenyl;
$R^{17}$ is lower alkyl or the group

$R^{18}$ is OH, O−Na+, lower alkyl or lower alkoxy; and the salts thereof of an organic base or an inorganic base.

The compounds of formula (C) are effective herbicidal agents against grasses and broad-leaved plants.

One embodiment of the present invention is shown by formula (A) below:

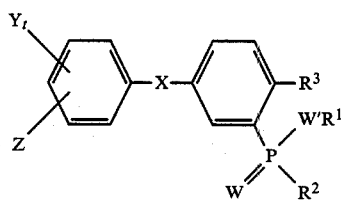
(A)

wherein, W' is oxygen, sulfur or amino; and $R^1$ is hydrogen, lower alkyl or aryl.

Synthesis of the compounds of formula (A) where W=oxygen, $R^3$=$NO_2$ and $R^1$=lower alkyl may be outlined as follows:

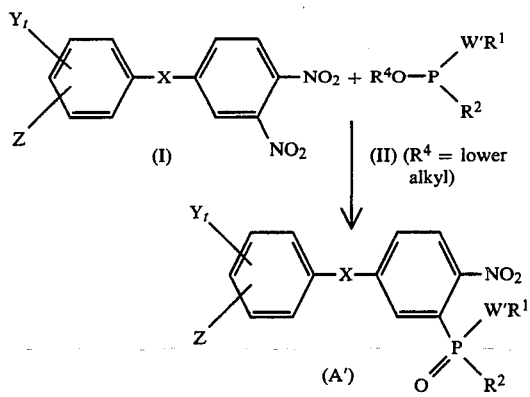

In the above synthesis, the dinitrobenzene (I) is phosphinylated with the phosphonite (II) at room temperature or at refluxing temperature to give the corresponding phosphinate (A'), following the procedure outlined by Cadogan et al., *J. Chem. Soc.*, (C):1314 (1969). The reaction can be carried out neat or in the presence of a solvent such as acetonitrile or tetrahydrofuran.

To produce the compounds of formula (A') where $R^1$=H, a phospinate (A') (where $R^1$=lower alkyl) is hydrolyzed by reaction with a strong acid such as hydrochloric acid or with trimethylsilyl bromide in methylene chloride or trichloromethane.

To synthesize the compounds of formula (A') where $R^1$=aryl, a phosphinate (A') (where $R^1$=lower alkyl) is halogenated by, for example, reaction with a compound such as thionyl chloride at reflux temperature, giving a phosphine oxide (III) (XX=Cl or Br).

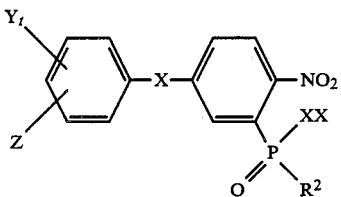

The phosphine oxide (or phosphinohalidate or phosphinic acid halide) (III) is reacted at reflux temperature with an alcohol $R^1$—OH (where $R^1$=aryl) in the presence of a base such as potassium carbonate and a solvent with high boiling point such as 2-butonone to give a phosphinate (A') where $R^1$=aryl.

The compounds of formula (A) where $R^3$=cyano or chloro can be produced by the hydrogenation of a phosphinate (A') to an amino compound (IV), which is diazotized following the procedure described in *Org. Synth. Coll.* Vol. 1:514 (1932). The diazo salt (V) is then reacted with cuprous cyanide or cuprous chloride.

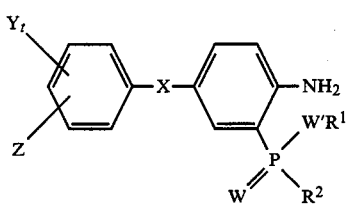

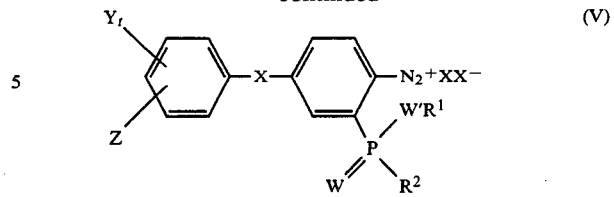

(XX = halogen)

To make the salts corresponding to formula (A), a phosphinic acid (formula A where $R^1$=H and W'=O) is reacted with an alkali metal hydroxide such as potassium hydroxide or sodium hydroxide in water to give a compound of formula (VI).

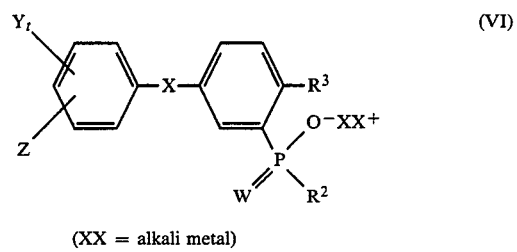

(XX = alkali metal)

Another embodiment of the present invention is shown by formula (B) below:

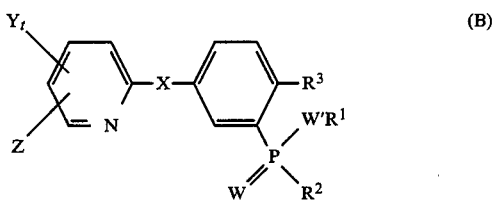

wherein, W' is oxygen, sulfur or amino; and $R^1$ is hydrogen, lower alkyl or aryl.

Compounds of formula (B) where W'=oxygen, $R^3$=NO$_2$ and $R^1$=lower alkyl may be prepared by the same procedures as described above for compounds of formula (A), following the below outlined synthesis:

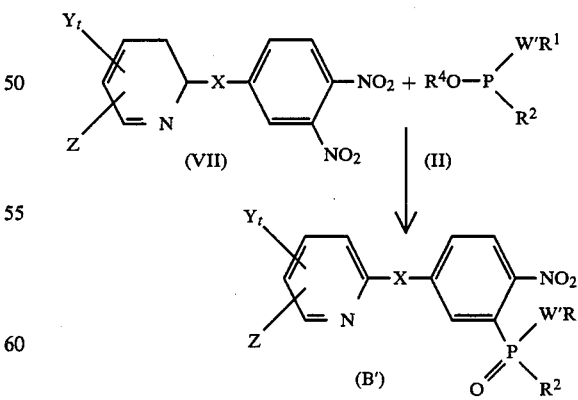

Compounds of formula (B) where W=oxygen, $R^3$=NO$_2$ and $R^1$=H; where W=oxygen, $R^3$=NO$_2$ and $R^1$=aryl; and where $R^3$=cyano or chloro may be synthesized by the procedures described above for corresponding compounds of formula (A). Likewise, the salts corresponding to formula (B) may also be prepared as described above.

Phosphinothioates of the present invention of formula (C) (where W=sulfur) can be prepared by reaction of a phosphinate (C where W=oxygen) with, for example, phosphorus pentasulfide at an elevated temperature.

The compounds of formula (C) where $R^5=OR^6$, $SR^7$ or $NHR^8$ may be prepared by reaction of a compound of formula (III') (prepared as described above for compound III) with an alcohol $HOR^6$, a thiol $HSR^7$ or an amine $NH_2R^8$ at room temperature or above in the presence of a solvent such as methylene chloride or tetrahydrofuran and with or without a base such as triethylamine or pyridine.

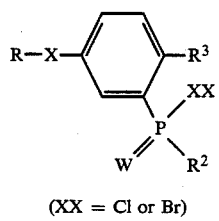

(XX = Cl or Br)

(III')

The following terms, wherever used in the description herein and in the appended claims, have the meaning defined below, unless otherwise specified hereinafter.

The term "lower alkyl" refers to an alkyl group, straight or branched, having a chains length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The term "lower alkylene" refers to an alkylene group, straight or branched, having a chain length of one to eight carbon atoms.

The term "lower alkenyl" refers to an ethylenically unsaturated hydrocarbon group, staight or branched, having a chain length of two to eight carbon atoms and one or two ethylenic bonds.

The term "lower alkynyl" refers to an alkynyl group, straight or branched, having a chain length of two to eight carbon atoms and one or two acetylenic bonds.

The term "lower cycloalkyl" refers to a cycloalkyl group of three to eight cyclic carbon atoms.

The term "aryl" refers to the aryl group phenyl or naphthyl. The terms "substituted aryl" and "substituted benzyl" refer to an aryl group and a benzyl group, respectively, substituted at one, two or three of the ring carbon atoms with a group selected from lower alkyl, lower haloalkyl, lower alkoxy, lower haloalkoxy, halogen, nitro, or cyano.

The term "lower alkoxyalkyl" refers to a lower alkyl group substituted with a lower alkoxy group.

The term "lower alkylthioalkyl" refers to a lower alkyl group substituted with a lower alkylthio group, straight or branched, having a chain length of one to eight carbon atoms.

The term "lower alkysulfonylalkyl" refers to a lower alkyl group substituted with a lower alkylsulfonyl group, straight or branched, of one to eight carbon atoms.

The term "lower alkylcarbonylalkyl" refers to a lower alkyl group substituted with a lower alkylcarbonyl group, straight or branched, or two to eight carbon atoms.

The term "dialkylaminoalkyl" refers to an aminoalkyl group, straight or branched, of one to eight carbon atoms wherein each of the two hydrogen atoms attached to the nitrogen atom is replaced by a lower alkyl group, as defined herein.

The term "phenoxyalkyl" refers to a lower alkyl group substituted with phenoxy.

The term "phenylthioalkyl" refers to a lower alkyl group substituted with phenylthio.

The term "phenylsulfonylalkyl" refers to a lower alkyl group substituted with phenylsulfonyl.

The terms "substituted phenoxyalkyl", "substituted phenylthioalkyl" and "substituted phenylsulfonylalkyl" refer to a phenoxyalkyl, a phenylthioalkyl and a phenylsulfonylalkyl group, respectively, substituted at one, two or three of the ring carbon atoms with a group selected from lower alkyl, lower haloalkyl, lower alkoxy, lower haloalkoxy, halogen, nitro or cyano.

The term "heterocycloalkyl" refers to a cycloalkyl group of three to eight cyclic carbon atoms wherein one ring carbon atom is replaced by an oxygen atom or a nitrogen atom. The term "heterocycloalkalkyl" refers to a heterocycloalkyl group as defined herein wherein one hydrogen atom is replaced by a lower alkyl group of one to four carbon atoms.

The compounds of formula (C) are useful for the control of weeds, using pre- and/or post-emergent treatments. The compounds can be applied in the form of dusts, granules, solutions, emulsions, wettable powders and suspensions. Application of a compound of the present invention is made according to conventional procedure to the weeds or their locus using an herbicidally effective amount of the compound, usually from about one-half or less to ten pounds per acre. Methods of preparing herbicidal formulations which can be used with a compound of the present invention are described in the literature along with suitable liquid and solid carriers such as in U.S. Pat. Nos. 4,192,669 and 4,163,661 which are incorporated herein by reference. The compounds of the present invention have herbicidal activity on both broad leaf plants and the grassy weeds or graminaceous weeds. The optimum usage of a compound of the present invention is readily determinable by one of ordinary skill in the art using routine testing such as greenhouse testing and small plot testing.

The term "herbicide," as used herein, refers to an active ingredient which modifies the growth of plants because of phytotoxic or plant growth regulating properties so as to retard the growth of the plant or damage sufficiently to kill it.

A preferred group of compounds of the present invention include the compounds of formula (B) hereinabove and the following compounds of formula (D):

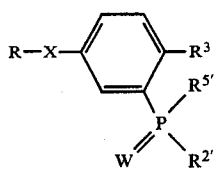

wherein:
R is the group

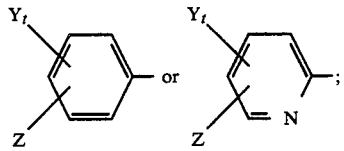

W is oxygen or sulfur;
X is oxygen, sulfur, amino or methylene;
Y is hydrogen, lower alkyl, lower alkoxy, lower haloalkyl, lower haloalkoxy, halogen, cyano or nitro;
Z is independently selected from the values of Y;
t is zero, one or two;
$R^{2'}$ is lower alkyl or aryl;
$R^3$ is cyano, nitro, amino or chloro;
$R^{5'}$ is hydrogen, —$OR^6$, —$SR^7$, or —$NHR^8$;
$R^6$ is lower alkenyl, lower alkynyl, lower haloalkenyl, lower haloalkynyl, cycloalkyl, cycloalkalkyl, substituted or unsubstituted aryl, substituted or unsubstituted benzyl, lower alkoxyalkyl, substituted or unsubstituted phenoxyalkyl, lower alkylthioalkyl, substituted or unsubstituted phenylthioalkyl, lower alkylcarbonylalkyl, lower alkylsulfonylalkyl, substituted or unsubstituted phenylsulfonylalkyl, dialkylaminoalkyl, heterocycloalkyl, heterocycloalkalkyl, lower alkoxycarbonylalkenyl, or the group

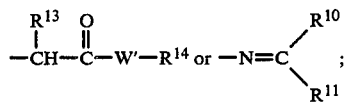

$R^7$ is lower alkenyl, lower alkynyl, aryl, or the group

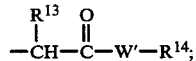

$R^8$ is lower alkenyl, lower alkynyl, aryl, or the group —$OR^{12}$ or —$NHR^{16}$ or

W' is oxygen or sulfur, or W'—$R^{14}$ is $NR^{15}R^{16}$;
$R^{10}$ is lower alkyl;
$R^{11}$ is lower alkyl, or together with $R^{10}$ forms a lower cycloalkyl ring;
$R^{12}$ is lower alkyl, lower alkenyl or lower alkynyl;
$R^{13}$ is hydrogen, lower alkyl, lower alkoxy or lower alkylthio;
$R^{14}$ is hydrogen, sodium, potassium, calcium, lower alkyl, lower haloalkyl, lower cyanoalkyl, lower alkoxyalkyl, lower alkenyl, lower haloalkenyl, lower alkynyl, lower alkylcarbonylalkyl, phenyl, substituted phenyl, benzyl, or the group

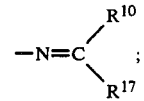

$R^{15}$ is hydrogen or lower alkyl;
$R^{16}$ is hydrogen, lower alkyl or substituted or unsubstituted phenyl; and
$R^{17}$ is lower alkyl or the group

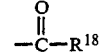

wherein $R^{18}$ is OH, $O^-Na^+$, lower alkyl or lower alkoxy.

The compounds of formulas (B) and (D) are useful herbicides, as described hereinabove for compounds of formula (C). Compounds of formula (D), such as methoxycarbonylmethyl P-ethyl-2-nitro-5-(2-chloro-4-trifluoromethylphenoxy)phenylphosphinate, show excellent broad spectrum pre- and post-emergence activity together with excellent tolerance for broadleaf plants such as soybeans and cotton when applied as a pre-emergent herbicide. Other compounds of formula (D) demonstrate post-emergent tolerance depending upon the choice of substituents.

The following examples are provided to illustrate the practice of the present invention. Temperature is given in degrees Centigrade.

EXAMPLE 1

A mixture of 4-(2-chloro-4-trifluoromethylphenoxy)-1,2-dinitrobenzene, (2-chloro-α,α,α-trifluoro-p-tolyl-3,4-dinitrophenyl ether) (1.2 g, 3.31 mmol) and dimethyl methylphosphonite (0.57 g, 5.3 mmol) in 3 ml of acetonitrile is refluxed overnight. The mixture is concentrated and the residue is purified by column chromatography (silica gel, eluting with 3% ethyl acetate/hexane) to yield methyl P-methyl-2-nitro-5-(2-chloro-4-trifluoromethylphenoxy)phenylphosphinate.

EXAMPLE 2

Following the procedure of Example 1, 1.5 g (4.14 mmol) of 4-(2-chloro-4-trifluoromethylphenoxy)-1,2-dinitrobenzene, 0.81 g (6.6 mmol) of dimethyl ethylphosphonite and 3 ml of acetonitrile are reacted together to give methyl P-ethyl-2-nitro-5-(2-chloro-4-trifluoromethylphenoxy)phenylphosphinate.

In like manner, diethyl ethylphosphonite is reacted with 4-(2-nitro-4-trifluoromethylphenoxy)-1,2-dinitrobenzene, yielding ethyl P-ethyl-2-nitro-5-(2-nitro-4-trifluoromethylphenoxy)phenyl phosphinate.

EXAMPLE 3

A solution of 1 g of methyl P-methyl-2-nitro-5-(2-chloro-4-trifluoromethylphenoxy)phenylphosphinate in 10 ml of 6N HCl is refluxed for 16 hours. After cooling, the solid product is collected by filtration and dried, yielding P-methyl-2-nitro-5-(2-chloro-4-trifluoromethylphenoxy)phenylphosphinic acid.

In like manner, methyl P-ethyl-2-nitro-5-(2-chloro-4-trifluoromethylphenoxy)phenylphosphinate is hydrolyzed to give P-ethyl-2-nitro-5-(2-chloro-4-trifluoromethylphenoxy)phenylphosphinic acid.

EXAMPLE 4

Following the procedure of Example 1, each of the compounds in column I is reacted with dimethyl methylphosphonite to give the phosphinates in column II.

I 4-(2,6-dichloro-4-trifluoromethylphenoxy)-1,2-dinitrobenzene
4-(4-chlorophenoxy)-1,2-dinitrobenzene
4-(4-trifluoromethylphenoxy)-1,2-dinitrobenzene
4-(2,4-dinitrophenoxy)-1,2-dinitrobenzene
4-(2-cyano-4-trifluoromethylphenoxy)-1,2-dinitrobenzene
4-(2,4,6-trichlorophenoxy)-1,2-dinitrobenzene
4-(2-methyl-4-methoxyphenoxy)-1,2-dinitrobenzene
4-(2-chloro-4-difluoromethoxyphenoxy)-1,2-dinitrobenzene
4-(2,4-dichlorophenoxy)-1,2-dinitrobenzene
4-(2-nitro-4-trifluoromethylphenoxy)-1,2-dinitrobenzene

II methyl P-methyl-2-nitro-5-(2,6-dichloro-4-trifluoromethylphenoxy)phenylphosphinate
methyl P-methyl-2-nitro-5-(4-chlorophenoxy)-phenylphosphinate
methyl P-methyl-2-nitro-5-(4-trifluoromethylphenoxy)-phenylphosphinate
methyl P-methyl-2-nitro-5-(2,4-dinitrophenoxy)phenylphosphinate
methyl P-methyl-2-nitro-5-(2-cyano-4-trifluoromethylphenoxy)phenylphosphinate
methyl P-methyl-2-nitro-5-(2,4,6-trichlorophenoxy)-phenylphosphinate
methyl P-methyl-2-nitro-5-(2-methyl-4-methoxyphenoxy)phenylphosphinate
methyl P-methyl-2-nitro-5-(2-chloro-4-difluoromethoxyphenoxy)phenylphosphinate
methyl P-methyl-2-nitro-5-(2,4-dichlorophenoxy)-phenylphosphinate
methyl P-methyl-2-nitro-5-(2-nitro-4-trifluoromethylphenoxy)phenylphosphinate

EXAMPLE 5

A solution of methyl P-methyl-2-nitro-5-(2-chloro-4-trifluoromethylphenoxy)phenylphosphinate (2 g, 5.5 mmol) in methanol (10 ml) is hydrogenated with 10% Pd/C (200 mg) at 1 atmosphere for 30 min. to give, after filtration and evaporation, methyl P-methyl-2-amino-5-(2-chloro-4-trifluoromethylphenoxy)phenylphosphinate. This is then diazotized following the procedure described in Org. Synth. Coll. Vol. 1, p. 514 (1932). The resulting diazo salt is treated with cuprous cyanide (1.2 eq.) in benzenewater solution. When the reaction is completed, the organic phase is separated, washed, dried and purified by thin layer chromatography to yield methyl P-methyl-2-cyano-5-(2-chloro-4-trifluoromethylphenoxy)phenylphosphinate.

EXAMPLE 6

A mixture of methyl P-methyl-2-nitro-5-(2-chloro-4-trifluoromethylphenoxy)phenylphosphinate (2 g) and an excess of thionyl chloride (10 ml) is refluxed for 3 hours. After removal of excess thionyl chloride, the resulting P-chloro-P-methyl-2-nitro-5-(2-chloro-4-trifluoromethylphenoxy)phenylphosphine oxide, in 5 ml of 2-butanone, is added to a solution of phenol (1.2 eq.) and potassium carbonate (1.5 eq.) in 20 ml of 2-butanone. The resulting mixture is refluxed under nitrogen for 24 hours, after which it is filtered and concentrated to dryness. Purification by chromatography (on silica gel, eluting with 3% ethyl acetate/hexane) yields phenyl P-methyl-2-nitro-5-(2-chloro-4-trifluoromethylphenoxy)phenylphosphinate.

EXAMPLE 7

P-methyl-2-nitro-5-(2-chloro-4-trifluoromethylphenoxy)phenylphosphinic acid (1 g) is combined with aqueous sodium hydroxide (1 eq.), with stirring at room temperature for 2 hours. The solution is then concentrated to dryness to yield the sodium salt of P-methyl-2-nitro-5-(2-chloro-4-trifluoromethylphenoxy)phenylphosphinic acid.

In the same way, P-ethyl-2-nitro-5-(2-chloro-4-trifluoromethylphenoxy)phenylphosphinic acid and aqueous sodium hydroxide are reacted to give the sodium salt of P-ethyl-2-nitro-5-(2-chloro-4-trifluoromethylphenoxy)phenylphosphinic acid.

EXAMPLE 8

A mixture of methyl P-methyl-2-nitro-5-(2-chloro-4-trifluoromethylphenoxy)phenylphosphinate (1.5 g, 4.7 mmol) and phosphorus pentasulfide (0.52 g, 1.2 mmol) is heated to 150°–160° under nitrogen for 3–4 hours. After cooling, the residue is purified by preparative thin-layer chromatography (on silica gel, eluting with 20% ethyl acetate/hexane) to give methyl P-methyl-2-nitro-5-(2-chloro-4-trifluoromethylphenoxy)phenylphosphinothioate.

In like manner, methyl P-ethyl-2-nitro-5-(2-chloro-4-trifluoromethylphenoxy)phenylphosphinothioate is prepared from methyl P-ethyl-2-nitro-5-(2-chloro-4-trifluoromethylphenoxy)phenylphosphinate and phosphorus pentasulfide.

EXAMPLE 9

Following the procedure of Example 1, 4-(2-chloro-4-trifluoromethylphenoxy)-1,2-dinitrobenzene and O-methyl-S-propyl methylphosphonite are reacted to yield S-propyl P-methyl-2-nitro-4-(2-chloro-4-trifluoromethylphenoxy)phenylphosphinothioate.

EXAMPLE 10

A mixture of P-chloro-P-methyl-2-nitro-5-(2-chloro-4-trifluoromethylphenoxy)phenyl-phosphine oxide (2 mmol) and ethylamine (3 mmol) in 10 ml of Toluene is heated at 50° overnight. Removal of the toluene by evaporation yields P-(N-ethylamino)-P-methyl-2-nitro-5-(2-chloro-4-trifluoromethylphenoxy)phenylphosphinate.

To prepare P-amino-P-ethyl-2-nitro-5-(2-chloro-4-trifluoromethylphenoxy)phenylphosphinate, ammonia gas is passed through P-chloro-P-ethyl-2-nitro-5-(2-chloro-4-trifluoromethylphenoxy)phenylphosphine oxide (2 mmol) in 10 ml of toluene, with heating at 50°. After reaction is complete, excess ammonia is removed and the toluene is evaporated off to give the final product.

EXAMPLE 11

A mixture of 4-(2-chloro-4-trifluoromethylphenoxy)-1,2-dinitrobenzene (0.9 g, 2.48 mmol), diethyl methylphosphonite (0.5 g, 3.72 mmol) and acetonitrile (3 ml) is stirred at room temperature overnight. The reaction mixture is concentrated to dryness, and the residue is purified by preparative thin layer chromatography (silica gel, eluting with 50% ethyl acetate/hexane) to give ethyl P-methyl-2-nitro-5-(2-chloro-4-trifluoromethylphenoxy)phenylphosphinate.

nmr (CDCl$_3$) δ 1.94–2.97 (6H, m, aromatic), 6.0 (2H, quint., P—OCH$_2$CH$_3$), 8.04 (3H, d, P—CH$_3$) and 8.75 ppm (3H, t, P—OCH$_2$CH$_3$).

EXAMPLE 12

Following the method of Example 11, 4-(2-chloro-4-trifluoromethylphenoxy)-1,2-dinitrobenzene (1.6 g, 4.4 mmol) and dimethyl ethylphosphonite (1 ml, 2 eq) in acetonitrile (6 ml) are reacted to yield, after purification by preparative thin layer chromatography (silica gel, 10% ethyl acetate/hexane), methyl P-ethyl-2-nitro-5-(2-chloro-4-trifluoromethylphenoxy)phenylphosphinate.

nmr (CDCl$_3$) δ 1.94–3.07 (6H, m, aromatic), 6.39 (3H, d, P—OCH$_3$), 7.84 (2H, quint., P—CH$_2$CH$_3$), 8.57 (3H, t, P—CH$_2$CH$_3$) and 8.90 ppm (3H, t, P—CH$_2$CH$_3$).

EXAMPLE 13

Ethyl P-methyl-2-nitro-5-(2-chloro-4-trifluoromethylphenoxy)phenylphosphinate (1 g) in 20 ml of 6N hydrochloric acid is heated under reflux overnight. The solution is then poured into water and extracted with methylene chloride. The combined solvent extracts are dried over magnesium sulfate and the solvent is then evaporated off to give P-methyl-2-nitro-5-(2-chloro-4-trifluoromethylphenoxy)phenylphosphinic acid.

nmr (CDCl$_3$) δ 2.0–3.17 (6H, m, aromatic) and 8.17 ppm (3H, d, P—CH$_3$).

EXAMPLE 14

Following the method of Example 13, 1 g of methyl P-ethyl-2-nitro-5-(2-chloro-4-trifluoromethyl-phenoxy)phenylphosphinate is reacted with 20 ml of 6N HCl to yield P-ethyl-2-nitro-5-(2-chloro-4-trifluoromethylphenoxy)phenylphosphinic acid, m.p.=99°.

EXAMPLE 15

A mixture of P-ethyl-2-nitro-5-(2-chloro-4-trifluoromethylphenoxy)phenylphosphinic acid (0.360 g, 0.91 mmol) and sodium hydroxide (0.364 g, 0.91 mmol) in 3 ml of water is stirred until a clear solution is obtained. The solution is then dried in vacuo to give the sodium salt of P-ethyl-2-nitro-5-(2-chloro-4-trifluoromethylphenoxy)phenylphosphinic acid.

EXAMPLE 16

Following the procedure of Example 1 or Example 11, dimethyl methylphosphonite is reacted with each of 4-(2-chloro-4-trifluoromethylphenylthio)-1,2-dinitrobenzene, 4-(2-chloro-4-trifluoromethylanilino)-1,2-dinitrobenzene and 4-(2-chloro-4-trifluoromethylbenzyl)-1,2-dinitrobenzene to yield, respectively,
methyl P-methyl-2-nitro-5-(2-chloro-4-trifluoromethylphenylthio)phenylphosphinate,
methyl P-methyl-2-nitro-5-(2-chloro-4-trifluoromethylanilino)phenylphosphinate, and
methyl P-methyl-2-nitro-5-(2-chloro-4-trifluoromethylbenzyl)phenylphosphinate.

EXAMPLE 17

Following the procedure of Example 1 or Example 11, each of 4-(2-chloro-4-trifluoromethylphenoxy)-1,2-dinitrobenzene and 4-(2,6-dichloro-4-trifluoromethylphenoxy)-1,2-dinitrobenzene is reacted with dimethyl P-n-propylphosphonite to yield, respectively,
methyl P-n-propyl-2-nitro-5-(2-chloro-4-trifluoromethylphenoxy)phenylphosphinate, and
methyl P-n-propyl-2-nitro-5-2,6-dichloro-4-trifluoromethylphenoxy)phenylphosphinate.

EXAMPLE 18

Following the method of Example 3 or Example 13, methyl P-n-propyl-2-nitro-5-(2-chloro-4-trifluoromethylphenoxy)phenylphosphinate and 6N HCl are reacted to give P-n-propyl-2-nitro-5-(2-chloro-4-trifluoromethylphenoxy)phenylphosphinic acid.

EXAMPLE 19

The sodium salt of P-n-propyl-2-nitro-5-(2-chloro-4-trifluoromethylphenoxy)phenylphosphinic acid is made by reacting P-n-propyl-2-nitro-5-(2-chloro-4-trifluoromethylphenoxy)phenylphosphinic acid and sodium hydroxide, following the procedure of Example 15.

EXAMPLE 20

Post-emergence herbicidal activity on the grasses (GR) green foxtail, watergrass, shattercane and wild oats and on the broadleafs (BL) annual morningglory, mustard, soybean and velvetleaf was tested for the compound of Examples 11, 12, 13, 14 and 15 (test compounds no. 1, 2, 3, 4 and 5) by spraying seedlings with a solution of water/acetone (1:1), surfactant (1%) and test compound at a rate equivalent to 10 lb/acre. The average score is given, in percent control, in Table I.

TABLE I

| Test Compound | GR | BL |
|---|---|---|
| 1 | 50 | 94 |
| 2 | 70 | 100 |
| 3 | 67 | 100 |
| 4 | 90 | 100 |
| 5 | 98 | 100 |

Pre-emergence herbicidal activity of test compounds 1, 2, 3, and 4 tested on the above grasses (GR) and broadleafs (BR-nightshade substituted for soybean) at a rate equivalent to 10 lb/acre. The average activity, in percent control, is given in Table II.

TABLE II

| Test Compound | GR | BL |
|---|---|---|
| 1 | 65 | 92 |
| 2 | 75 | 93 |
| 3 | 77 | 85 |
| 4 | 93 | 88 |

EXAMPLE 21

Following the procedure of Example 11, 4-(3-chloro-5-trifluoromethyl-2-pyridyloxy)-1,2-dinitrobenzene is reacted with each of dimethyl ethylphosphonite, diethyl methylphosphonite and dimethyl n-propylphosphonite to yield, respectively,
methyl P-ethyl-2-nitro-5-(3-chloro-5-trifluoromethyl-2-pyridyloxy)phenylphosphinate,
ethyl P-methyl-2-nitro-5-(3-chloro-5-trifluoromethyl-2-pyridyloxy)phenylphosphinate, and
methyl P-n-propyl-2nitro-5-(3-chloro-5-trifluoro methyl-2-pyridyloxy)phenylphosphinate.

EXAMPLE 22

Following the method of Example 13, each of the phosphinate products of Example 21 is reacted with 6N HCl to give, respectively,
P-ethyl-2-nitro-5-(3-chloro-5-trifluoromethyl-2-pyridyloxy)phenylphosphinic acid,
P-methyl-2-nitro-5-(3-chloro-5-trifluoromethyl-2-pyridyloxy)phenylphosphinic acid, and
P-n-propyl-2-nitro-5-(3-chloro-5-trifluoromethyl-2-pyridyloxy)phenylphosphinic acid.

EXAMPLE 23

Following the procedure of Example 1 or Example 11, each of 4-(5-chloro-2-pyridyloxy)-1,2-dinitrobenzene, 4-(3,5-dichloro-2-pyridyloxy)-1,2-dinitrobenzene and 4-(5-trifluoromethyl-2-pyridyloxy)-1,2-dinitrobenzene is reacted with dimethyl ethylphosphonite to yield, respectively,
methyl P-ethyl-2-nitro-5-(5-chloro-2-pyridyloxy)phenylphosphinate,
methyl P-ethyl-2-nitro-5-(3,5-dichloro-2-pyridyloxy)phenylphosphinate, and
methyl P-ethyl-2-nitro-5-(5-trifluoromethyl-2-pyridyloxy)phenylphosphinate.

EXAMPLE 24

Following the procedure of Example 15, the sodium salt of
P-ethyl-2-nitro-5-(3-chloro-5-trifluoromethyl-2-pyridyloxy)phenylphosphinic acid, each of
P-methyl-2-nitro-5-(3-chloro-5-trifluoromethyl-2-pyridyloxy)phenylphosphinic acid, and
P-n-propyl-nitro-5-(3-chloro-5-trifluoromethyl-2-pyridyloxy)phenylphosphinic acid is prepared by reacting each of the acids with sodium hydroxide.

EXAMPLE 25

P-methyl-2-nitro-5-(2-chloro-4-trifluoromethylphenoxy)phenylphosphinic acid (350 mg) and thionyl chloride (3 ml) are heated under reflux for 1.5 hours. Excess thionyl chloride is removed and the remaining P-methyl-2-nitro-5-(2-chloro-4-trifluoromethylphenoxy)phenylphosphino-chloridate is dissolved in 10 ml of methylene chloride. To this solution is passsed an excess of methylamine at 0° for 2 minutes. The reaction is then taken up in methylene chloride, washed with brine, dried and evaporated to dryness to yield N-methyl P-methyl-2-nitro-5-(2-chloro-4-trifluoromethylphenoxy)phenylphosphinamide, M.P.=150°–151°.

In the same manner, P-ethyl-2-nitro-5-(2-chloro-4-trifluoromethylphenoxy)phenylphosphinic acid is reacted with thionyl chloride, and the resulting phosphinochloridate is reacted with methylamine to give N-methyl P-ethyl-2-nitro-5-(2-chloro-4-trifluoromethylphenoxy)phenylphosphinamide, hygroscopic.

nmr (CDCl$_3$) δ 1.87–2.13 (6H, m, aromatic), 7.43–7.64 (3H, dd, P—NHCH$_3$), 7.90 (2H, quint., P—CH$_2$CH$_3$) and 8.80–9.14 ppm (3H, tt, P—CH$_2$CH$_3$).

EXAMPLE 26

To a mixture of P-ethyl-2-nitro-5-(2-chloro-4-trifluoromethylphenoxy)phenylphosphinochloridate (2 mmol), methylene chloride (2 mmol) and triethylamine (2 mmol) is added allylamine (3 mmol). The mixture is stirred at room temperature for about 2 hours. The reaction is then taken up in methylene chloride, washed with brine, dried and evaporated, yielding N-allyl P-ethyl-2-nitro-5-(2-chloro-4-trifluoromethylphenoxy)phenylphosphinamide.

In like manner, P-ethyl-2-nitro-5-(2-chloro-4-trifluoromethylphenoxy)phenylphosphinochloridate is reacted with each of the amines in column III to give the corresponding phosphinamide in column IV.

III

O-allylhydroxyamine
propargylamine
phenylamine
N-methylsulfonamine
2-chloroethylamine

IV

N-(O-allylhydroxy) P-ethyl-2-nitro-5-(2-chloro-4-trifluoromethylphenoxy)phenylphosphinamide
N-propargyl P-ethyl-2-nitro-5-(2-chloro-4-trifluoromethylphenoxy)phenylphosphinamide
N-phenyl P-ethyl-2-nitro-5-(2-chloro-4-trifluoromethylphenoxy)phenylphosphinamide
N-methylsulfonyl P-ethyl-2-nitro-5-(2-chloro-4-trifluoromethylphenoxy)phenylphosphinamide
N-(2-chloroethyl) P-ethyl-2-nitro-5-(2-chloro-4-trifluoromethylphenoxy)phenylphosphinamide

EXAMPLE 27

Following the procedure of Example 26, but without the inclusion of triethylamine, each of ethyl 2-hydroxypropanoate and ethyl thioethanoate is reacted with P-ethyl-2-nitro-5-(2-chloro-4-trifluoromethylphenoxy)phenylphosphinochloridate to yield, respectively, α-(ethoxycarbonylethyl) P-ethyl-2-nitro-5-(2-chloro-4-trifluoromethylphenoxy)phenylphosphinate and S-α-(ethoxycarbonylethyl) P-ethyl-2-nitro-5-(2-chloro-4-trifluoromethylphenoxy)phenylphosphinothioate.

EXAMPLE 28

Following the procedure of Example 26, each of acetone oxime and cyclohexanone oxime is reacted with P-methyl-2-nitro-5-(2-chloro-4-trifluoromethylphenoxy)phenylphosphinochloridate to give, respectively, dimethylidene P-methyl-2-nitro-5-(2-chloro-4-trifluoromethylphenoxy)phenylphosphinoxime ester, m/s 464 (M+), and cyclohexylidene P-methyl-2-nitro-5-(2-chloro-4-trifluoromethylphenoxy)phenylphosphinoxime ester.

EXAMPLE 29

Following the procedure of Example 1, a mixture of 4-(2-chloro-4-trifluoromethylphenoxy)-1,2-dinitrobenzene (2.0 g, 5.52 mmol) and dimethyl phenylphosphonite (1.4 g, 8.28 mmol) in 4 ml of acetonitrile is heated under reflux overnight. The crude product is purified to yield methyl P-phenyl-2-nitro-5-(2-chloro-4-trifluoromethylphenoxy)phenylphosphinate, m/s 471 (M+).

EXAMPLE 30

P-ethyl-2-nitro-5-(2-chloro-4-trifluoromethylphenoxy)phenylphosphinochloridate (2 mmol) is added to a solution of methyl copper, prepared from copper (I) oxide (4.4 mmol) in tetrahydrofuran (40 ml) and methyllithium (4 mmol) at −20°. The mixture is stirred at −20° for 2 hours, then allowed to warm to RT and treated with dilute hydrochloric acid and extracted with methylene chloride. The combined extracts are washed, dried and evaporated to dryness to give P- methyl-P-ethyl-2-nitro-5-(2-chloro-4-trifluoromethyl-phenoxy)phenylphosphinate.

EXAMPLE 31

A mixture of 4-(2-chloro-4-trifluoromethylphenoxy)-1,2-dinitrobenzene (1.8 g, 4.97 mmol), sodium hypophosphite (0.88 g, 9.94 mmol) and cupric sulfate (180 mg) in 20 ml of methyl nitrile/water (4:1) is heated under reflux for 24 hours. The reaction is poured into water, extracted with methylene chloride, dired and chromatographed (silica gel, eluting with 10% methanol/chloroform) to yield 2-nitro-5-(2-chloro-4-trifluoromethylphenoxy)phenylphosphinic acid.

EXAMPLE 32

A mixture of P-ethyl-2-nitro-5-(2-chloro-4-trifluoromethylphenoxy)phenylphosphinic acid (500 mg), potassium carbonate (300 mg) and methyl bromoacetate (400 mg) in 2-butanone (10 ml) is heated under reflux for 1 hour. The reaction is filtered and concentrated, and the crude product is purified by prep. TLC to yield methoxycarbonylmethyl P-ethyl-2-nitro-5-(2-chloro-4-trifluoromethylphenoxy)phenylphosphinate.

nmr (CDCl$_3$) δ 5.67 (d, 2H, 10.5 Hz,

6.34 (s, 3H, —OCH$_3$), 7.70 (sextet, 2H, —PCH$_2$CH$_3$) and 8.65 ppm (tt, 3H, —P CH$_2$CH$_3$).

In the same way, P-ethyl-2-nitro-5-(2-fluoro-4-trifluoromethylphenoxy)phenylphosphinic acid is reacted with methyl bromoacetate to give methoxycarbonylmethyl P-ethyl-2-nitro-5-(2-fluoro-4-trifluoromethylphenoxy)phenylphosphinate.

EXAMPLE 33

A mixture of P-ethyl-2-nitro-5-(2-chloro-4-trifluoromethylphenoxy)phenylphosphinic acid (700 mg, 1.86 mmol), potassium carbonate (309 mg, 1.2 eq) and methyl 2-bromopropionate (467 mg, 1.5 eq.) in acetone (20 ml) is heated under reflux for 24 hours. After filtration and concentration, the oily residue is purified by prep. TLC (40% ethyl acetate/hexane) to give α-(methoxy carbonylethyl) P-ethyl-2-nitro-5-(2-chloro-4-trifluoromethylphenoxy)-phenylphosphinate. P nmr (CDCl$_3$) δ 5.07 (m, 1H,

6.43–6.23 (ss, 3H, —OCH$_3$), 7.70 (m, 2H, —PCH$_2$CH$_3$), 8.64–8.44 (dd, 3H, 7 Hz,

and 9.00–8.65 (tt,3H, —PCH$_2$CH$_3$).

In the same manner, P-ethyl-2-nitro-5-(2-chloro-4-trifluoromethylphenoxy)phenylphosphinic acid (500 mg., 1.22 mmol) and ethyl bromoacetate (408 mg, 2.44 mmol) are reacted together with potassium carbonate (253 mg, 1.83 mmol) in 2-butanone (10 ml) to yield ethoxycarbonylmethyl P-ethyl-2-nitro-5-(2-chloro-4-tri-fluoromethylphenoxy)phenylphosphinate.

nmr (CDCl$_3$)δ 5.40 (d, 2H, 10.5 Hz,

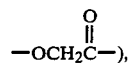

5.87 (q, 2H, —OCH$_2$CH$_3$), 7.70 (sextet, 2H, —PCH$_2$CH$_3$), 8.76 (t, 3H, —OCH$_2$CH$_3$) and 8.65 (t, 3H, —PCH$_2$CH$_3$).

EXAMPLE 34

Following the above procedures, P-ethyl-2-nitro-5-(2-chloro-4-trifluoromethylphenoxy)-phenylphosphinic acid is reacted with each of isopropyl bromoacetate and t-butyl bromoacetate to yield, respectively, isopropoxycarbonylmethyl P-ethyl-2-nitro-5-(2-chloro-4-trifluoromethylphenoxy)phenyl-phosphinate [nmr (CDCl$_3$) δ 4.97 (m, 1H, —OCH(CH$_3$)$_2$), 5.45 (d, 2H,

7.70 (sextet, 2H, —P—CH$^2$CH$_3$), 8.84–8.70 (ss, 6H, —OCH(CH$_3$)$_2$) and 9.00–8.65 ppm (tt, 3H, —PCH$_2$CH$_3$)], and t-butoxycarbonylmethyl P-ethyl-2-nitro-5-(2-chloro-4-trifluoromethylphenoxy)phenylphosphinate [nmr (CDCl$_3$) δ 5.57 (d, 10.5 Hz,

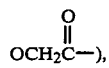

7.70 (sextet, 2H. —PCH$_2$CH$_3$), 8.57 (s, 9H, —OC(CH$_3$)$_3$) and 9.00–8.65 (tt, 2H, —PCH$_2$CH$_3$)].

EXAMPLE 35

Following the procedure of Example 32, P-ethyl-2-nitro-5-(2-chloro-4-trifluoromethylphenoxy)phenylophosphinic acid is reacted with each of the carboxylates or carboxythioates in column V to give the corresponding posphinate in column VI.

V 1. ethyl 2-bromopropionate
2. cyanomethyl bromoacetate
3. n-butyl bromoacetate
4. phenyl bromoacetate
5. 4-chlorophenyl bromoacetate
6. benzyl bromoacetate
7. bromoacetic acid
8. methyl bromoacetothioate
9. benzyl bromoacetothioate
10. allyl bromoacetate
11. 2-propynyl bromoacetate
12. 2,2,2-trifluoroethyl bromoacetate
13. 3,3-dichloro allyl bromoacetate
14. acetonyl bromoacetate
15. 2-(bromoacetoxyimino)acetone
16. methyl 2-(bromoacetoxyimino)propionate
17. 2-(bromoacetoxyimino)-3-pentanone
18. 2-(bromoacetoxyimino)propionic acid
19. ethyl methylthiobromoacetate
20. methyl methoxybromoacetate
21. sec-butyl bromoacetate

VI

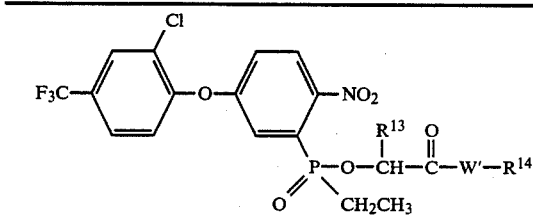

| | R13 | W' | R14 | |
|---|---|---|---|---|
| 1. | CH3 | O | CH2CH3 | m/s 509 (M+) |
| 2. | H | O | CH2CN | |
| 3. | H | O | CH2CH2CH2CH3 | |
| 4. | H | O | C6H5 | |
| 5. | H | O | (4-Cl)C6H4 | |
| 6. | H | O | CH2C6H5 | m/s 557 (M+) |
| 7. | H | O | H | m/s 481 (M+) |
| 8. | H | S | CH3 | |
| 9. | H | S | CH2C6H5 | |
| 10. | H | O | CH2CH=CH2 | m/s 507 (M+) |
| 11. | H | O | CH2C≡CH | |
| 12. | H | O | CH2CF3 | |
| 13. | H | O | CH2CH=C(Cl)2 | |
| 14. | H | O | CH2C(O)CH3, | m/s 523 (M+) |
| 15. | H | O | N=C(CH3)2, | m/s 522 (M+) |
| 16. | H | O | N=C(CH3) (COOCH3) | |
| 17. | H | O | N=C(CH3) (C(O)CH2CH3) | |
| 18. | H | O | N=C(CH3) (COOH) | |
| 19. | SCH3 | O | CH2CH3 | |
| 20. | OCH3 | O | CH3 | |
| 21. | H | O | CH(CH3)CH2CH3, | m/s 523 (M+) |

EXAMPLE 36

Following the procedure of Example 32, each of the compounds bromoacetamide, N,N-dimethyl bromoacetamide, N-methyl-N-phenylbromoacetamide, and N-ethyl bromoacetamide is reacted with P-ethyl-2-nitro-5-(2-chloro-4-trifloromethylphenoxy)-phenylphosphinic acid to yield, respectively, amidocarbonylmethyl P-ethyl-2-nitro-5-(2-chloro-4-trifluoromethylphenoxy)phenylphosphinate, N,N-dimethylamidocarbonylmethyl P-ethyl-2-nitro-5-(2-chloro-4-trifluoromethylphenoxy)phenylphosphinate, N-methyl-N-phenylamidocarbonylmethyl P-ethyl-2-nitro-5-(2-chloro-4-trifluoromethylphenoxy)phenylphosphinate, and ethylamidocarbonylmethyl P-ethyl-2-nitro-5-(2-chloro-4-trifluoromethylphenoxy)phenylphosphinate.

EXAMPLE 37

Following the procedures of Example 20, the compound methoxycarbonylmethyl P-ethyl-2-nitro-5-(2-chloro-4-trifluoromethylphenoxy)phenylphosphinate was tested for both pre-emergence and post-emergence herbicidal activity.

The average pre-emergence activity of the compound in percent control was 95% in grasses and 100% in broadleafs.

The compound showed 100% post-emergent control in both grasses and broadleafs.

EXAMPLE 38

Following the procedure of Example 11, 4-(2-fluoro-4-trifluoromethylphenoxy)-1,2-dinitrobenzene is reacted with each of diethyl methylphosphonite and dimethyl ethylphosphonite to yield, respectively, ethyl P-methyl-2-nitro-5-(2-fluoro-4-trifluoromethylphenoxy)phenylphosphinate, and methyl P-ethyl-2-nitro-5-(2-fluoro-4-trifluoromethylphenoxy)phenylphosphinate.

Following the procedure of Example 13, methyl P-ethyl-2-nitro-5-(2-fluoro-4-trifluoromethylphenoxy)-phenylphosphinate is reacted with 6N HCl to give P-ethyl-2-nitro-5-(2-fluoro-4-trifluoromethylphenoxy)-phenylphosphinic acid.

EXAMPLE 39

Following the procedure of Example 32, methyl bromoacetate is reacted with each of P-ethyl-2-nitro-5-(2,6-dichloro-4-trifluoromethylphenoxy)phenylphosphinic acid, P-ethyl-2-nitro-5-(4-trifluoromethylphenoxy)phenylphosphinic acid, P-ethyl-2-nitro-5-(4-chlorophenoxy)phenylphosphinic acid and P-ethyl-2-nitro-5-(4-chloro-2-nitrophen oxy)phenylphosphinic acid to yield, respectively, methoxycarbonylmethyl P-ethyl-2-nitro-5-(2,6-dichloro-4-trifluoromethylphenoxy)phenylphosphinate, methoxycarbonylmethyl P-ethyl-2-nitro-5-(4-trifluoromethylphenoxy)phenylphosphinate, methoxycarbonylmethyl P-ethyl-2-nitro-5-(4-chlorophenoxy)phenylphosphinate, and methoxycarbonylmethyl P-ethyl-2-nitro-5-(4-chloro-2-nitrophenoxy)phenylphosphinate.

EXAMPLE 40

Following the procedure of Example 32, P-ethyl-2-nitro-5-(3-chloro-5-trifluoromethyl-2-pyridyloxy)-phenylphosphinic acid is reacted with each of the carboxylates in column VII to give the corresponding phosphinate in column VIII.

VII methyl bromoacetate
isopropyl bromoacetate
t-butyl bromoacetate
methyl 2-bromopropionate
bromoacetic acid
2,2,2-trifluoroethyl bromoacetate

VIII methoxycarbonylmethyl P-ethyl-2-nitro-5-(3-chloro-5-trifluoromethyl-2-pyridyloxy)-phenylphosphinate
isopropoxycarbonylmethyl P-ethyl-2-nitro-5-(3-chloro-5-trifluoromethyl-2-pyridyloxy)phenylphosphinate
α-(t-butoxycarbonylethyl)P-ethyl-2-nitro-5-(3-chloro-5-trifluoromethyl-2-pyridyloxy)phenylphosphinate
α-(methoxycarbonylethyl)P-ethyl-2-nitro-5-(3-chloro-5-trifluoromethyl-2-pyridyloxy)phenylphosphinate
hydroxycarbonylmethyl P-ethyl-2-nitro-5-(3-chloro-5-trifluoromethyl-2-pyridyloxy)phenylphosphinate
2,2,2-trifluoroethoxycarbonylmethyl P-ethyl-2-nitro-5-(3-chloro-5-trifluoromethyl-2-pyridyloxy)phenylphosphinate

EXAMPLE 41

Following the procedure of Example 15, each of hydroxycarbonylmethyl P-ethyl-2-nitro-5-(2-chloro-4-trifluoromethylphenoxy)-phenylphosphinate and hydroxycarbonylmethyl P-ethyl-2-nitro-5-(3-chloro-5-trifluoromethyl-2-pyridyloxy)phenylphosphinate is reacted with sodium hydroxide to give the sodium salt of each of the two compounds.

EXAMPLE 42

Following the procedure of Example 11, 4-(2-chloro-4-trifluoromethylphenoxy)-1,2-dinitro-benzene is reacted with each of diethyl n-propylphosphonite, diethyl isopropylphosphonite, diethyl t-butylphosphonite and diethyl sec-butyl-phosphonite to yield, respectively,
ethyl-P-n-propyl-2-nitro-5-(2-chloro-4-trifluoromethyl-phenoxy)phenylphosphinate, m/s 451 (M+);
ethyl P-isopropyl-2-nitro-5-(2-chloro-4-trifluoromethylphenoxy)phenylphosphinate, m/s 451 (M+);
ethyl P-t-butyl-2-nitro-5-(2-chloro-4-trifluoromethyl-phenoxy)phenylphosphinate, m/s 465 (M+); and
ethyl P-sec-butyl-2-nitro-5-(2-chloro-4-trifluoromethyl-phenoxy)phenylphosphinate, m/s 465 (M+).

Following the procedure of Example 13, each of the above phosphinates is hydrolyzed to yield, respectively,
P-n-propyl-2-nitro-5-(2-chloro-4-trifluoro-methyl-phenoxy)phenylphosphinic acid, m/s 423 (M+);
P-isopropyl-2-nitro-5-(2-chloro-4-trifluoro-methyl-phenoxy)phenylphosphinic acid, m/s 423 (M+);
P-t-butyl-2-nitro-5-(2-chloro-4-trifluoromethyl-phenoxy)phenylphosphinic acid, m/s 437 (M+); and
P-sec-butyl-2-nitro-5-(s-chloro-4-trifluoro-methyl-phenoxy)phenylphosphinic acid, m/s 437 (M+).

EXAMPLE 43

Following the procedure of Example 11, 4-(2,4-dichlorophenoxy)-1,2-dinitrobenzene is reacted with dimethyl methylphosphonite to give methyl P-methyl-2-nitro-5-(2,4-dichloro-phenoxy)phenylphosphinate, m/s 376 (M+).

In the same way dimethyl ethylphosphonite is reacted with each of 4-(2,4-dichlorophenoxy)-1,2-dinitrobenzene, 4-(4-bromo-2-chlorophenoxy)-1,2-dinitrobenzene and 4-(4-trifluoromethylphenoxy)-1,2-dinitrobenzene to give, respectively,
methyl P-ethyl-2-nitro-5-(2,4-dichlorophenoxy)-phenylphosphinate, m/s 390 (M+);
methyl P-ethyl-2-nitro-5-(4-bromo-2-chloro-phenoxy)-phenylphospinate, m/s 435 (M+); and
methyl P-ethyl-2-nitro-5-(4-trifluoromethyl-phenoxy)-phenylphosphinate, m/s 389 (M+).

Following the procedure of Example 13, each of the above four phosphinates is hydrolyzed to yield, respectively,
P-methyl-2-nitro-5-(2,4-dichlorophenoxy)-phenylphosphinic acid, m/s 362 (M+);
P-ethyl-2-nitro-5-(2,4-dichlorophenoxy)phenyl-phosphinic acid, m/s 375 (M+);
P-ethyl-2-nitro-5-(4-bromo-2-chlorophenoxy)phenyl-phosphinic acid, m/s 420 (M+); and
P-ethyl-2-nitro-5-(4-trifluoromethylphenoxy)phenyl-phosphinic acid.

EXAMPLE 44

Following the procedure of Example 32, P-ethyl-2-nitro-5-(2-chloro-4-trifluoromethyl-phenoxy)phenyl-phosphinic acid is reacted with each of the compounds under column IX to give the corresponding phosphinate under column X.

IX 22. chloroacetonitrile
23. chloropropiononitrile
24. 2-chloroethyl bromide
25. 3,3-dichloro-2-propenyl bromide
26. 2-propenyl bromide
27. 2-(4-bromophenoxy)ethyl bromide
28. 2-phenylthioethyl chloride
29. t-butylcarbonylmethyl bromide
30. chloroacetone
31. chloroacetophenone

X

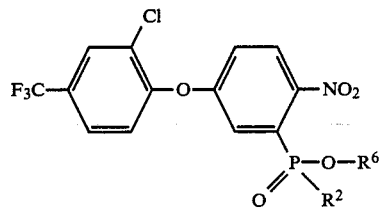

| | $R^2$ | $R^6$ | m/s (M+) |
|---|---|---|---|
| 22. | $CH_2CH_3$ | $CH_2CN$ | 448 |
| 23. | $CH_2CH_3$ | $CH_2CH_2CN$ | 462 |
| 24. | $CH_2CH_3$ | $CH_2CH_2Cl$ | 457 |
| 25. | $CH_2CH_3$ | $C=C(Cl)_2$ | 518 |
| 26. | $CH_2CH_3$ | $CH_2CH=CH_2$ | 449 |
| 27. | $CH_2CH_3$ | $CH_2CH_2OC_6H_4(4-Br)$ | 608 |
| 28. | $CH_2CH_3$ | $CH_2CH_2SC_6H_5$ | 545 |
| 29. | $CH_2CH_3$ | $CH_2C(O)C(CH_3)_3$ | 507 |
| 30. | $CH_2CH_3$ | $CH_2C(O)CH_3$ | 465 |
| 31. | $CH_2CH_3$ | $CH_2C(O)C_6H_5$ | 503 |

EXAMPLE 45

To P-ethyl-2-nitro-5-(2-chloro-4-trifluoro-methylphenoxy)phenylphosphinic acid chloride, prepared from P-ethyl-2-nitro-5-(2-chloro-4-trifluoromethylphenoxy)-phenylphosphinic acid (500 mg, 1.22 mmol) and thionyl chloride (3 ml) by the procedure of Example 25, in methylene chloride (3 ml) is added propargyl alcohol (3 ml) and triethyl amine (0.2 ml). The mixture is stirred at RT for 4 hours, after which the reaction is taken up in methylene chloride, washed, dried and evaporated. The crude product is purified by prep. TLC to give propargyl P-ethyl-2-nitro-5-(2-chloro-4-trifluoromethylphenoxy)phenylphosphinate, m/s 447 (M+).

In the same way, P-ethyl-2-nitro-5-(2-chloro-4-trifluoromethylphenoxy)phenyl-phosphinic acid chloride is reacted with each of the alcohols under column XI to yield the corresponding phosphinate under column XII.

XI 32. 4-chlorobenzyl alcohol
33. 2-(4-nitrophenylthio)-1-ethanol
34. 2-methylthio-1-ethanol
35. 2-ethylthio-1-ethanol
36. 2-methoxy-1-ethanol
37. 2,3-epoxy-1-propanol
38. 2,5-epoxy-1-pentanol
39. 1,4-epoxy-2-butanol
40. 2-(N,N-dimethylamino)-1-ethanol

XII

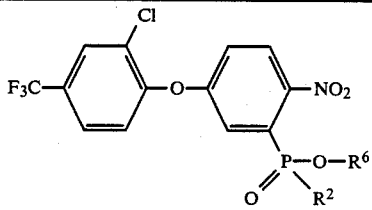

| | R² | R⁶ | m/s (M+) |
|---|---|---|---|
| 32. | CH₂CH₃ | CH₂C₆H₄(4-Cl) | 534 |
| 33. | CH₂CH₃ | CH₂CH₂SC₆H₄(4-NO₂) | 590 |
| 34. | CH₂CH₃ | CH₂CH₂SCH₃ | 483 |
| 35. | CH₂CH₃ | CH₂CH₂SCH₂CH₃ | 483 |
| 36. | CH₂CH₃ | CH₂CH₂OCH₃ | 453 |
| 37. | CH₂CH₃ | CH₂CH⟨CH₂/O⟩ | 465 |
| 38. | CH₂CH₃ | CH₂CHCH₂CH₂CH₂ (O) | 493 |
| 39. | CH₂CH₃ | CHCH₂CH₂ / CH₂—O | 479 |
| 40. | CH₂CH₃ | CH₂CH₂N(CH₃)₂ | 480 |

EXAMPLE 46

A. A solution of methyl P-methyl-2-nitro-5-(2-chloro-4-trifluoromethylphenoxy)phenylphosphinate (1.8 g) in ethanol (10 ml) with 10% Pd/C (0.3 g) is hydrogenated at 30 lb. pressure at RT for about 1.5 hours to give, after filtration and evaporation, methyl P-methyl-2-amino-5-(2-chloro-4-trifluoromethylphenoxy)phenyl-phosphinate.

The above aminophenylphosphinate, in 2 ml of ethanol, is added dropwise to HBF₄ (3 ml) which has been cooled to 0°. Sodium nitrite (0.34 g), dissolved in 2 ml of water and cooled to 0°, is added dropwise to the mixture to give the diazo salt of the phosphinate.

Cuprous chloride (1.2 eq.) is dissolved in a minimum of 2N HCl/CH₃CN and is then added dropwise to the above diazo salt at 0°. After addition is complete, the reaction mixture is allowed to warm to RT and is extracted with ether. The combined extracts are dried and the crude product is purified by prep. TLC (silica gel, developing with 50% ethyl acetate/hexane, then with 50% acetone/hexane) to give methyl P-methyl-2-chloro-5-(2-chloro-4-trifluoromethylphenoxy)phenyl-phosphinate, m/s 398 (M+).

B. A solution of 90% pure sodium cyanide (895 mg) in a minimum of water is added to a stirring suspension of cuprous chloride (660 mg) in 2 ml of water, cooled to 0°. The diazo salt from A above, neutralized with sodium carbonate, is added dropwise to the cuprous cyanide system. The reaction mixture is stirred for 2 hours and is then extracted with ether. The combined extracts are washed and dried, and the crude product is purified by prep. TLC to give methyl P-methyl-2-cyano-5-(2-chloro-4-trifluoromethylphenoxy)phenylphosphinate, m/s 389 (M+).

C. To a solution of methyl P-methyl-2-cyano-5-(2-chloro-4-trifluoromethylphenoxy)-phenylphosphinate (0.46 g) in 10 ml of methylene chloride is added trimethylsilyl bromide (0.75 ml) dropwise. The mixture is stirred for 2 hours, after which methanol is added. The reaction is stripped and evaporated under vacuum to give P-methyl-2-cyano-5-(2-chloro-4-trifluoromethylphenoxy)phenylphosphinic acid, m/s 375 (M+).

Methyl P-methyl-2-chloro-5-(2-chloro-4-trifluoromethylphenoxy)phenylphosphinate is reacted in the same manner as above to give P-methyl-2-chloro-5-(2-chloro-4-trifluoromethylphenoxy)phenylphosphinic acid, m/s 384 (M+).

EXAMPLE 47

Following the procedure of Example 46, ethyl P-ethyl-2-amino-5-(2-chloro-4-trifluoro-methylphenoxy)-phenylphosphinate is prepared from ethyl P-ethyl-2-nitro-5-(2-chloro-4-trifluoromethylphenoxy)phenylphosphinate, and is then diazotized. The resulting diazo salt is reacted with each of cuprous cyanide and cuprous chloride to yield, respectively, ethyl P-ethyl-2-cyano-5-(2-chloro-4-trifluoromethylphenoxy)phenylphosphinate, m/s 417 (M+); and ethyl P-ethyl-2-chloro-5-(2-chloro-4-trifluoromethylphenoxy)phenylphosphinate, m/s 426 (M+).

Each of the above phosphinates is reacted with trimethylsilyl bromide and then with methanol, again following the procedure of Example 46, to give, respectively, P-ethyl-2-cyano-5-(2-chloro-4-trifluoromethylphenoxy)phenyphosphinic acid, and P-ethyl-2-chloro-5-(2-chloro-4-trifluoromethylphenoxy)phenylphosphinic acid, m/s 399 (M+).

EXAMPLE 48

Following the procedure of Example 45, P-methyl-2-nitro-5-(2-chloro-4-trifluoromethylphenoxy)phenylphosphinic acid chloride and propargylamine are reacted together to give N-propargyl P-methyl-2-nitro-5-(2-chloro-4-trifluoromethylphenoxy)phenylphosphinamide, m/s 432 (M+).

EXAMPLE 49

Following the procedure of Example 45, P-ethyl-2-nitro-5-(2-chloro-4-trifluoromethylphenoxy)phenylphosphinic acid chloride and 2,3-(dimethylmethylenedioxy)-1-propanol are reacted together to yield 2,3-(dimethylmethylenedioxy)propyl P-ethyl-2-nitro-5-(2-chloro-4-trifluoromethylphenoxy)phenylphosphinate, m/s 523 (M+).

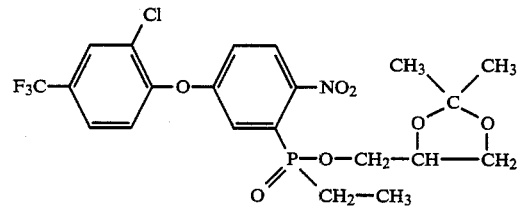

EXAMPLE 50

2-Amino-3,5-dichloropyridine (21.0 g.) is dissolved in conc. HCl (200 ml.), then cooled with ice. To this solution, NaNO₂ (48 g.) in water (60 ml.) is added slowly over 30 minutes. The reaction mixture is stirred at 0° for 1 hour and then 50° for 1 hour. The mixture is then poured into ice-water and extracted with ether. The combined extracts are washed, dried and evaporated to dryness to give yellow solid. The solid is stirred with 25% ether/hexane and filtered. The filtrate is concentrated and washed again with 25% ether/hexane to give 2,3,5-trichloropyridine (12 g.).

A mixture of the above trichloropyridine (6 g.), m-nitrophenol (4.58 g.), K₂CO₃ (5.4 g.) and DMSO (25 ml.) is heated to 120° for 16 hours. The mixture is poured into water and extracted with ether. The combined extracts are washed, dried and evaporated to crystalline solid. The solid is crystallized from ether/hexane (25/50) to yield 4-(3,5-dichloropyridyloxy)-2-nitrobenzene.

To a solution of the above mono-nitro ether (1.5 g.) in CH₂Cl₂ (3 ml.) is added conc. H₂SO₄ (8 ml.) at 0° and KNO₃ (760 mg.) in portions. The mixture is stirred at 0° for 1 hour and then R.T. for 2 hours. The mixture is poured onto ice and extracted with CH₂Cl₂. The combined extracts are washed, dried and evaporated to dryness and washed with ether to give 4-(3,5-dichloro-2-pyridyloxy)-1,2-dinitrobenzene (yield 1.45 g.).

EXAMPLE 51

A mixture of 4-(3,5-dichloro-2-pyridyloxy)-1,2-dinitrobenzene (1.4 g., 4.48 mmol), dimethyl ethylphosphinate (1.1 ml., 8.96 mmol) and acetonitrile (10 ml.) is stirred at RT overnight. The reaction mixture is evaporated to dryness, and the resulting residue is purified by prep. TLC to give methyl P-ethyl-2-nitro-5-(3,5-dichloro-2-pyridyloxy)phenylphosphinate.

nmr (CDCl₃)+acetone-d₆) δ 1.80–2.54 (m, 6H, aromatic H), 6.34 (d, 3H, 12 Hz, OCH₃), 7.87 (sextet, 2H, PCH₂CH₃) and 8.60–9.04 ppm (tt, 3H, PCH₂CH₃).

A mixture of methyl P-ethyl-2-nitro-5-(3,5-dichloro-2-pyridyloxy)phenylphosphinate (0.6 g.), methanol (10 ml.) and 5% aqueous potassium hydroxide (10 ml.) is heated to 90° for 15 min. The basic aqueous solution is acidified and extracted with ether. The combined ether extracts are washed and dried and the solvent is evaporated off to give P-ethyl-2-nitro-5-(3,5-dichloro-2-pyridyloxy)phenyl-phosphinic acid.

nmr (CDCl₃)+acetone-d₆) δ 1.20 (bs, 1H, POH), 1.80–2.50 (m, 6H, aromatic H), 7.77 (sextet, 2H, PCH₂CH₃) and 8.80–9.14 ppm (tt, 3H, PCH₂CH₃).

A mixture of P-ethyl-2-nitro-5-(3,5-dichloro-2-pyridyloxy)phenylphosphinic acid (0.42 g., 1.2 mmol), potassium carbonate (2.0 mg), methyl bromoacetate (0.2 ml., 2.4 mmol), and 2-butanone (20 ml.) is heated under reflux for 2 hours. The reaction mixture is filtered and concentrated, and the crude product is purified by prep. TLC (50% ethyl acetate/hexane) to give methoxycarbonylmethyl P-ethyl-2-nitro-5-(3,5-dichloro-2-pyridyloxy)phenylphosphinate.

nmr (CDCl₃) δ 1.74–2.64 (m, 6H, aromatic H), 5.44 (d, 2H, 12 Hz, POCH₂—), 6.30 (s, 3H, —OCH₃), 7.92 (sextet, 2H, PCH₂CH₃) and 8.64–8.97 ppm (tt, 3H, PCH₂CH₃).

EXAMPLE 52

Following the procedure of Example 32, P-ethyl-2-nitro-5-(2-chloro-4-trifluoromethyl-phenoxy)phenylphosphinic acid is reacted with each of the carboxylates under column XIII to give the corresponding phosphinates under column XIV.

XIII 41. trimethylsilylethyl bromoacetate
42. ethoxycarbonylethyl bromoacetate
43. 2,5-epoxypentyl bromoacetate
44. 3-methoxy-3-methylbutyl bromoacetate
45. isopentyl bromoacetate
46. 3,3-dimethylbutyl bromoacetate
47. pentamethylbenzyl chloride

XIV

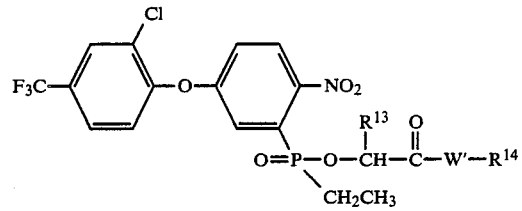

| | R¹³ | W' | R¹⁴ | m/s (M⁺) |
|---|---|---|---|---|
| 41. | H | O | CH₂CH₂Si(CH₃)₃ | 567 |
| 42. | H | O | CH(CH₃)C(O)OCH₂CH₃ | 567 |
| 43. | H | O | CH₂CHCH₂CH₂CH₂ (epoxide) | 551 |
| 44. | H | O | CH₂CH₂C(CH₃)₂OCH₃ | 567 |
| 45. | H | O | CH₂CH₂CH(CH₃)₂ | 532 |
| 46. | H | O | CH₂C(CH₃)₃ | 551 |
| 47. | H | O | CH₂C₆(CH₃)₅ | 583 |

EXAMPLE 53

Following the procedure of Example 45, P-methyl-2-nitro-5-(2-chloro-4-trifluoromethyl-phenoxy)phenylphosphinic acid chloride is reacted with each of ethyl lactate and 3,3-dimethylbutanol to give, respectively, α-(ethoxycarbonylethyl) P-methyl-2-nitro-5-(2-chloro-4-trifluoromethoxyphenoxy)phenylphosphinate, m/s 495 (M⁺); and 3,3-dimethylbutyl P-methyl-2-nitro-5-(2-chloro-4-trifluoromethylphenoxy)phenylphosphinate, m/s 448 (M⁺).

In the same way, P-ethyl-2-nitro-5-(2-chloro-4-trifluoromethylphenoxy)phenylphosphinic acid chloride is reacted with each of the alcohols, thiols or amines listed under column XV to give the corresponding phosphinates under column XVI.

XV 48. 4-chlorophenol
49. methoxyethoxyethanol
50. hydrogen sulfide
51. 2,6-dichlorohydrazine
52. methoxycarbonyl-2-propenol

XVI

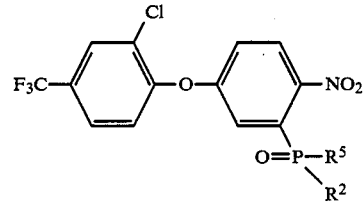

| | R² | R⁵ | m/s (M⁺) |
|---|---|---|---|
| 48. | CH₂CH₃ | OC₆H₄(4-Cl) | 519 |
| 49. | CH₂CH₃ | OCH₂CH₂OCH₂CH₂OCH₃ | 511 |
| 50. | CH₂CH₃ | SH | 425 |
| 51. | CH₂CH₃ | NHNHC₆H₃(2,6-diCl) | 568 |

-continued

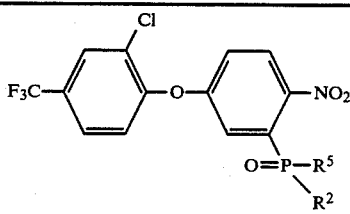

| | $R^2$ | $R^5$ | m/s (M+) |
|---|---|---|---|
| 52. | $CH_2CH_3$ | $OCH_2CH=CHC(O)OCH_3$ | 507 |

EXAMPLE 54

A mixture of methylthioethyl P-ethyl-2-nitro-5-(2-chloro-4-trifluoromethylphenoxy)-phenylphosphinate (480 mg, 1.0 mmol), 3-chloroperbenzoic acid (600 mg, 3.5 mmol) and chloroform (5 ml) is stirred at RT overnight. The reaction mixture is diluted with chloroform, washed with 5% potassium hydroxide (2×), dried and filtered, and the solvent is stripped off. The crude product is purified on the chromatotron (developing with ethyl acetate) to give methylsulfonylethyl P-ethyl-2-nitro-5-(2-chloro-4-trifluoromethylphenoxy)phenylphosphinate, m/s 515 (M+).

In the same way, phenylthioethyl P-ethyl-2-nitro-5-(2-chloro-4-trifluoromethylphenoxy)phenylphosphinate (630 mg, 1.15 mmol) and 3-chloroperbenzoic acid (600 mg, 3.5 mmol) are reacted together to give phenylsulfonylethyl P-ethyl-2-nitro-5-(2-chloro-4-trifluoromethylphenoxy)phenylphosphinate, m/s 577 (M+).

EXAMPLE 55

Following the procedure of Example 13, methyl P-phenyl-2-nitro-5-(2-chloro-4-trifluoromethylphenoxy)-phenylphosphinate is hydrolyzed to give P-phenyl-2-nitro-5-(2-chloro-4-trifluoromethylphenoxy)phenylphosphinic acid, m/s 457 (M+).

EXAMPLE 56

Emulsifiable concentrates are prepared having the following compositions (components in percent by weight):

| (#3) | Compound B | 27.78 |
|---|---|---|
| | Igepol CO-530 | 2.67 |
| | Tween 21 | 2.67 |
| | Tween 81 | 2.67 |
| | Corn Oil | 64.21 |

Compound B is the compound of Example 32, first paragraph. Tween 21 is a non-ionic surfactant, polyoxyethylene sorbitan monolaurate, and Tween 81 is a non-ionic surfactant, polyoxyethylene sorbitan monooleate. "Tween" is a trademark of ICI Americas. Igepol CO-530 is a non-ionic surfactant, monylphenoxy-poly(ethyleneoxy)ethanol, of GAF, Inc.

| (#4) | Compound C | 29.3 |
|---|---|---|
| | Toximol S | 6.4 |
| | Atlox 8916 TF | 1.6 |
| | Tenneco 500-100 | 62.7 |

Compound C is the second compound of Example 34. Toximol S is a surfactant of the Stepan Chemical Corporation, Illinois. Atlox 8916 TF is a surfactant of ICI, Americas, Delaware. Tenneco 500-100 is an aromatic solvent of the Tenneco Corporation.

EXAMPLE 57

Flowable formulations are prepared having the following compositions (components in percent by weight):

| (#8) | (A) | Compound B | 3.00 |
|---|---|---|---|
| | | Toximol 360A | 3.00 |
| | | Sun 7N (oil) | 30.00 |
| | (B) | Water | 60.85 |
| | | Gelvatol 20/30 | 3.00 |
| | | Kelzan | 0.15 |

Premix (A) is dispersed in a high-speed blender for about one minute, and then premix (B) is poured into premix (A) while stirring at high speed. Stirring is continued for about 5 minutes.

Toximol 360A is a surfactant of the Stepan Chemical Corporation. Sun 7N is a non-phytotoxic oil of the Sun Chemical Company. Gelvatol 20/30 is a polyvinyl alcohol, molecular weight about 10,000, of the Monsanto Company. Kelzan is a thickening agent (xanthum gum).

| (#9) | (A) | Compound C | 3.00 |
|---|---|---|---|
| | | Toximol 360A | 3.00 |
| | | Sun 7A | 30.00 |
| | (B) | Water | 60.85 |
| | | Gelvatol 20/30 | 3.00 |
| | | Darvan No. 1 | 0.15 |

Premix (A) and (B) are combined as described for flowable formulation #8 above. Darvan No. 1 is a dispersant of the RT Vanderbilt Company.

EXAMPLE 58

Following the procedure of Example 11, 4-(2-nitro-4-trifluoromethylanilino)-1,2-dinitrobenzene and dimethyl ethylphosphonite are reacted together to give methyl P-ethyl-2-nitro-5-(2-nitro-4-trifluoromethylanilino)-phenylphosphinate.

Methyl P-ethyl-2-nitro-5-(2-nitro-4-trifluoromethylanilino)phenylphosphinate is then hydrolyzed, following Example 13 procedures, to P-ethyl-2-nitro-5-(2-nitro-4-trifluoromethylanilino)phenylphosphinic acid.

Following the procedure of Example 32, P-ethyl-2-nitro-5-(2-nitro-4-trifluoromethyl-anilino)phenylphosphinic acid is reacted with methylbromoacetate to give methoxycarbonylmethyl P-ethyl-2-nitro-5-(2-nitro-4-trifluoromethylanilino)phenylphosphinate.

Examples of herbicides which can be combined with the compounds of the present invention are described by W. T. Thomson, "Agricultural Chemicals-Book II Herbicides," Thomson Publications, Fresno, Calif., U.S., 1981–82 Revision, such as alachlor or metribuzin.

What is claimed is:

1. A compound of the following formula:

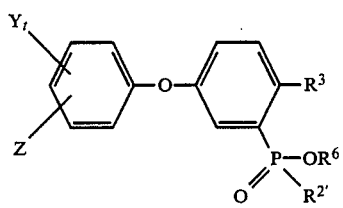

wherein,
Y is hydrogen, lower alkyl, lower alkoxy, lower haloalkyl, lower haloalkoxy, halogen, cyano or nitro;
Z is independently selected from the values of Y;
t is zero, one or two;
$R^{2'}$ is lower alkyl or aryl;
$R^3$ is cyano or nitro;
$R^6$ is lower alkenyl, lower alkynyl, lower haloalkenyl, lower haloalkynyl, lower alkoxyalkyl, lower alkylthioalkyl, or the group

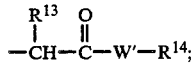

W' is oxygen or sulfur;
$R^{13}$ is hydrogen or lower alkyl; and
$R^{14}$ is hydrogen, sodium, potassium, calcium, lower alkyl, lower haloalkyl, lower alkoxyalkyl, lower alkenyl, lower haloalkenyl, lower alkynyl or lower alkylcarbonylalkyl.

2. A compound according to claim 1 of the formula:

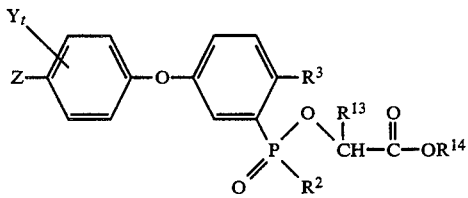

wherein,
t is one or two;
Y is chloro, said Y being in the 2 position or 2, 6 positions;
Z is chloro or trifluoromethyl;
$R^2$ is methyl or ethyl;
$R^3$ is nitro or cyano;
$R^{13}$ is hydrogen or methyl; and
$R^{14}$ is hydrogen, methyl, ethyl, isopropyl, t-butyl or sodium.

3. A compound according to claim 1 of the formula:

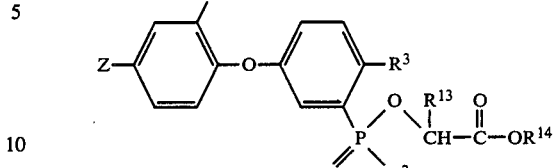

wherein,
Y is chloro, fluoro or nitro;
Z is chloro or trifluoromethyl;
$R^2$ is methyl or ethyl;
$R^3$ is nitro or cyano;
$R^{13}$ is hydrogen or methyl; and
$R^{14}$ is hydrogen, methyl, ethyl, isopropyl, t-butyl or sodium.

4. A compound according to claim 1 of the formula:

wherein Y is hydrogen or chloro; Z is chloro or trifluoromethyl; $R^3$ is nitro or cyano; $R^2$ is methyl or ethyl; $R^{13}$ is hydrogen or methyl; and $R^{14}$ is hydrogen, lower alkyl, benzyl, lower alkenyl or lower alkylcarbonylalkyl.

5. A compound according to claim 4 wherein $R^{14}$ is hydrogen or lower alkyl.

6. A compound according to claim 4 wherein Y is chloro, Z is trifluoromethyl, $R^3$ is nitro, $R^2$ is ethyl, $R^{13}$ is hydrogen and $R^{14}$ is allyl.

7. A compound according to claim 4 wherein Y is chloro, Z is trifluoromethyl, $R^3$ is nitro, $R^2$ is ethyl, $R^{13}$ is hydrogen and $R^{14}$ is hydrogen.

8. The compound methoxycarbonylmethyl P-ethyl-2-nitro-5-(2-chloro-4-trifluoromethylphenoxy)phenylphosphinate.

9. The compound, propargyl P-ethyl-2-nitro-5-(2-chloro-4-trifluoromethylphenoxy)phenylphosphinate.

10. The compound, ethylthioethyl P-ethyl-2-nitro-5-(2-chloro-4-trifluoromethylphenoxy)phenylphosphinate.

* * * * *